US009879222B2

(12) United States Patent
Didion et al.

(10) Patent No.: US 9,879,222 B2
(45) Date of Patent: Jan. 30, 2018

(54) GENDER-SPECIFIC SEPARATION OF SPERM CELLS AND EMBRYOS

(75) Inventors: Bradley Didion, Mount Horeb, WI (US); Whitney Erwin, Oregon, WI (US); Reiner Bleher, Madison, WI (US)

(73) Assignee: MofA Group LLC, Shawano, WI (US)

( * ) Notice: Subject to any disclaimer, the term of this patent is extended or adjusted under 35 U.S.C. 154(b) by 564 days.

(21) Appl. No.: 12/747,988

(22) PCT Filed: Dec. 15, 2008

(86) PCT No.: PCT/US2008/086833
§ 371 (c)(1),
(2), (4) Date: Jun. 30, 2010

(87) PCT Pub. No.: WO2009/079456
PCT Pub. Date: Jun. 25, 2009

(65) Prior Publication Data
US 2010/0311059 A1 Dec. 9, 2010

Related U.S. Application Data

(60) Provisional application No. 61/013,901, filed on Dec. 14, 2007.

(51) Int. Cl.
*C12Q 1/68* (2006.01)
*C12N 5/071* (2010.01)

(52) U.S. Cl.
CPC ......... *C12N 5/0612* (2013.01); *C12Q 1/6879* (2013.01); *C12Q 1/6839* (2013.01)

(58) Field of Classification Search
CPC ................ C12Q 1/6839; C12Q 1/6879; C12Q 2525/107; C12Q 2537/119
See application file for complete search history.

(56) References Cited

U.S. PATENT DOCUMENTS

| | | |
|---|---|---|
| 3,687,803 A | 8/1972 | Grayson |
| 3,894,529 A | 7/1975 | Shrimpton |
| 4,009,260 A | 2/1977 | Ericsson |
| 4,067,965 A | 1/1978 | Bhattacharya |
| 4,083,957 A | 4/1978 | Lang |
| 4,085,205 A | 4/1978 | Hancock |
| 4,092,229 A | 5/1978 | Bhattacharya |
| 4,155,831 A | 5/1979 | Bhattacharya |
| 4,191,749 A | 3/1980 | Bryant |
| 4,225,405 A | 9/1980 | Lawson |
| 4,276,139 A | 6/1981 | Lawson |
| 4,339,434 A | 7/1982 | Ericsson |
| 4,362,246 A | 12/1982 | Adair |
| 4,448,767 A | 5/1984 | Bryant |
| 4,511,661 A | 4/1985 | Goldberg |
| RE32,350 E | 2/1987 | Bhattacharya |
| 4,680,258 A | 7/1987 | Hammerling et al. |
| 4,698,142 A | 10/1987 | Muroi et al. |
| 4,749,458 A | 6/1988 | Muroi et al. |
| 4,999,283 A | 3/1991 | Zavos et al. |
| 5,021,244 A | 6/1991 | Spaulding |
| 5,135,759 A | 8/1992 | Johnson |
| 5,176,996 A | 1/1993 | Hogan et al. |
| 5,215,884 A | 6/1993 | McGraw |
| 5,346,990 A | 9/1994 | Spaulding |
| 5,439,362 A | 8/1995 | Spaulding |
| 5,514,537 A | 5/1996 | Chandler |
| 5,514,786 A | 5/1996 | Cook et al. |
| 5,539,082 A | 7/1996 | Nielsen et al. |
| 5,623,068 A | 4/1997 | Reddy et al. |
| 5,660,997 A | 8/1997 | Spaulding |
| 5,844,110 A | 12/1998 | Gold |
| 5,892,024 A | 4/1999 | Chaturvedula et al. |
| 5,962,426 A | 10/1999 | Glazer |
| 5,985,216 A | 11/1999 | Rens et al. |
| 6,071,689 A | 6/2000 | Seidel et al. |
| 6,149,867 A | 11/2000 | Seidel et al. |
| 6,263,745 B1 | 7/2001 | Buchanan et al. |
| 6,524,860 B1 | 2/2003 | Seidel et al. |
| 6,610,839 B1 | 8/2003 | Morin et al. |
| 7,002,006 B2 | 2/2006 | Song et al. |
| 7,037,654 B2 | 5/2006 | Chenna et al. |
| 7,053,207 B2 | 5/2006 | Wengel |
| 7,084,125 B2 | 8/2006 | Wengel et al. |
| 7,094,527 B2 | 8/2006 | Seidel et al. |
| 7,195,920 B2 | 3/2007 | Seidel et al. |

(Continued)

FOREIGN PATENT DOCUMENTS

| | | |
|---|---|---|
| CA | 2598805 | 8/2006 |
| EP | 1334109 | 5/2006 |
| EP | 2149605 | 2/2010 |
| JP | 2000-32999 | 2/2000 |
| WO | WO 89/01978 | 3/1989 |
| WO | WO 90/15155 | 12/1990 |
| WO | WO 1996/23777 | 8/1996 |
| WO | WO 1999/33956 | 7/1999 |

(Continued)

OTHER PUBLICATIONS

McGraw et al; Nucleic Acids Research, vol. 16, pp. 10389; 1988.*
Rufer et al; Nature Biotechnology; vol. 16, pp. 743-747; 1998.*
Perez-Lezaun et al; J Mol. Evol, vol. 45, pp. 265-270, 1997.*
Mujumdar et al, Bioconjugate Chemistry, vol. 4, 1993, pp. 105-111.*
Li et al; JACS 2005, vol. 127, pp. 12657-12665.*
Nielsen and Egholm; Current Issues Molec. Biol. 1999; vol. 1, pp. 89-104.*
Bleasdale, C. et al., "4,4'-Dimethoxytrityl and 4-Monomethoxytrityl Tetrafluoroborate: Convenient Reagents for the Protection of Primary Alcohols Including Sugars" J. Chem. Soc., Perkins Trans. 1 (1990) pp. 803-805.

(Continued)

*Primary Examiner* — Jehanne S Sitton
(74) *Attorney, Agent, or Firm* — Brian L. Stender; Patterson Thuente Pedersen, P.A.

(57) ABSTRACT

Disclosed are sperm cells or embryos comprising a labeled oligonucleotide bound to a gender-specific repeat sequence. Methods for separating sperm cells or embryos containing a labeled oligonucleotide from sperm cells not containing the labeled oligonucleotide produce gender-enriched sperm cell fractions. The separated fractions are useful in producing offspring of a predetermined sex.

16 Claims, 3 Drawing Sheets

(56) References Cited

U.S. PATENT DOCUMENTS

| | | | |
|---|---|---|---|
| 7,202,036 | B2 | 4/2007 | Cai et al. |
| 7,276,599 | B2 | 10/2007 | Moore et al. |
| 7,282,575 | B2 | 10/2007 | Ikeda et al. |
| 7,449,571 | B2 | 11/2008 | Gold |
| 7,572,582 | B2 | 8/2009 | Wengel et al. |
| 7,575,863 | B2 | 8/2009 | Chen et al. |
| 7,741,294 | B1 | 6/2010 | Benner |
| 7,803,580 | B2 | 9/2010 | Millar |
| 8,057,997 | B2 | 11/2011 | Seela et al. |
| 8,153,365 | B2 | 4/2012 | Wengel et al. |
| 2003/0032794 | A1 | 2/2003 | Koch et al. |
| 2003/0087230 | A1 | 5/2003 | Wengel |
| 2003/0113765 | A1* | 6/2003 | Dempcy et al. ............ 435/6 |
| 2003/0198982 | A1 | 10/2003 | Seela et al. |
| 2003/0224377 | A1 | 12/2003 | Wengel et al. |
| 2004/0142946 | A1 | 7/2004 | Chattopadhyaya |
| 2004/0219565 | A1 | 11/2004 | Kauppinen et al. |
| 2005/0026192 | A1 | 2/2005 | Moore et al. |
| 2005/0053939 | A1 | 3/2005 | Chenna et al. |
| 2005/0266418 | A1 | 12/2005 | Chen et al. |
| 2005/0287566 | A1 | 12/2005 | Wengel et al. |
| 2006/0172315 | A1* | 8/2006 | Anderson et al. ............ 435/6 |
| 2007/0117144 | A1 | 5/2007 | Kauppinen et al. |
| 2009/0317817 | A1 | 12/2009 | Oeth et al. |
| 2010/0121135 | A1 | 5/2010 | Oksenberg et al. |
| 2010/0190172 | A1 | 7/2010 | Cargill et al. |
| 2010/0210712 | A1 | 8/2010 | Hansen et al. |
| 2010/0223691 | A1 | 9/2010 | Bundock |
| 2010/0273999 | A1 | 10/2010 | Jung et al. |
| 2010/0311059 | A1 | 12/2010 | Didion et al. |
| 2010/0317004 | A1 | 12/2010 | Bunce et al. |
| 2011/0021365 | A1 | 1/2011 | Seela et al. |
| 2011/0137010 | A1 | 6/2011 | Srivastava et al. |
| 2011/0287415 | A1 | 11/2011 | Fan et al. |
| 2012/0040857 | A1 | 2/2012 | Kingston et al. |

FOREIGN PATENT DOCUMENTS

| | | |
|---|---|---|
| WO | WO 00/56748 | 9/2000 |
| WO | WO 2001/37655 | 5/2001 |
| WO | WO 02/12263 | 2/2002 |
| WO | WO 2002/41906 | 5/2002 |
| WO | WO 03/020877 | 3/2003 |
| WO | WO 03/039523 | 5/2003 |
| WO | WO 03/052132 | 6/2003 |
| WO | WO 03/052133 | 6/2003 |
| WO | WO 03/052134 | 6/2003 |
| WO | WO 2006/012597 | 2/2006 |
| WO | WO 2007/104318 | 9/2007 |
| WO | WO 2008/028081 | 3/2008 |
| WO | WO 2008/061311 | 5/2008 |
| WO | WO 2009/064115 | 5/2009 |
| WO | WO 2009/079456 | 6/2009 |
| WO | WO 2010/003420 | 1/2010 |
| WO | WO 2011/103468 | 8/2011 |
| WO | WO 2011/117353 | 9/2011 |
| WO | WO 2013/103713 | 7/2013 |

OTHER PUBLICATIONS

Comins, D. et al., "Regioselective Lithium—Halogen Xxchange and Palladium-Catalyzed Cross-Coupling Reactions of 2,4-dihaloquinolines" Tetra. Lett. (2005) 46:6697-6699.

Coppola, G.M., "The Chemistry of Isatoic Anhydride" Synthesis (1980) pp. 556-536.

Didion, Bradley A. et al., "Boar Fertility and Sperm Chromatin Structure Status: A Retrospective Report," J. Andrology; (2009); 30:6:655-660.

Evans, D. et al., "Directed Reduction of B-Hydroxy Ketones Employing Tetramethylammonium Triacetoxyborohydride" J. Am. Chem. Soc. (1988) 110:3560-3578.

Fonvielle et al., "Decoding the Logic of the tRNA Regiospecificity of Nonribosomal FemXWv Aminoacyl Transferase" Angew. Chem. Int. Ed. 2010, 49, 5115-5119.

Fukuda et al., "Duplex formation of multiple pyrene-modified RNAs" Nucleic Acids Symposium Series No. 53, 2009, 133-134.

Gaboreanu, A-M. et al., "Characterization of an X-Chromosome PCR-RFLP Marker Associated with Fat Deposition and Growth in the Pig," Animal Genetics (2004) 35(5):401-403.

Gupta et al., "Synthesis and Biophysical Studies of Coronene Functionalized 2'-Amino-LNA: A Novel Class of Fluorescent Nucleic Acids" Bioconjugate Chem. 2010, 21, 513-520.

Kadin, S. et al., "A Convenient Synthesis of 2-Amino-4-hydroxyquinolines" Synthesis (1977) 1977:500-501.

Kalra et al., "Conformationally controlled high-affinity targeting of RNA or DNA by novel 2'-amino-DNA/LNA mixmers and pyrenyl-functionalized 2'-amino-DNA" Org. Biomol. Chem., 2004, 2, 2885-2887.

Klapars, A. et al., "Copper-Catalyzed Halogen Exchange in Aryl Halides: An Aromatic Finkelstein Reaction" J. Am. Chem. Soc. (2002) 124:14844-14845.

Kumar et al., "2'-N-(Pyren-l-yl)acetyl-2'-Amino-a-LLNA:Synthesis and Detection of Single Nucleotide Mismatches in DNA and RNA Targets" ChemBioChem 2007, 8, 1122-1125.

Kumar et al., "Functionalized 2'-Amino-r-L-LNA: Directed Positioning of Intercalators for DNA Targeting" J. Org. Chem. 2009, 74, 1070-1081.

Kumar et al., "Synthesis and Biophysical Studies of N2'-Functionalized 2'-Amino-α-L-LNA" Nucleosides, Nucleotides, and Nucleic Acids, 26:1403-1405, 2007.

Kumar et al., "Nucleic Acid Structural Engineering Using Pyrene-Functionalized 2'-Amino-r-L-LNA Monomers and Abasic Sites" dated J. Org. Chem. 2008, 73, 7060-7066.

Kumar et al., "Parallel RNA-strand recognition by 20-amino-b-L-LNA" Bioorganic & Medicinal Chemistry Letters 19 (2009) 2396-2399.

Lan, T. et al., "Synthesis of a dA-dT Base Pair Analogue and its Effects on DNA-Ligand Binding." Bioorg. Chem. (2001) 29:198-210.

Larsen, E. et al., "A New and Easy Synthesis of Silylated Furanoid Glycals in One Step from Nucleosides" Synthesis (1994) 1994:10:1037-1038.

Li, J-S et al., "Design of Triple Helix Forming C-Glycoside Molecules," J. Am. Chem. Soc. (2003) 125:2084-2093.

Li, J-S et al., "Molecular Recognition via Triples Formation of Mixed Purine/Pyrimidine DNA Sequences Using OligoTRIPs," J. Am. Chem. Soc. (2005) 127:12657-12665.

Li, J-S et al., "Synthesis of C-Nucleosides Designed to Participate in Triplex Formation with Native DNA: Specific Recognition of an A:T Base Pair in DNA," J. Org. Chem. (2005) 70:8764-8771.

Li, J-S et al., "Triple Helix Forming TRIPside Molecules That Target Mixed Purine/Pyrimidine DNA Sequences," Biochemistry (2004) 43:1440-1448.

Mahara et al., "Detection of Acceptor Sites for Antisense Oligonucleotides on Native Folded RNA by Fluorescence Spectroscopy" Bioorganic & Medicinal Chemistry 11 (2003) 2783-2790.

Mahara et al., "Detection of Acceptor Sites for Antisense Oligonucleotides on Native Folded RNA by Fluorescence-Labeled Oligonucleotide" Nucleic Acids Research Supplement No. 3 (2003) 73-74.

Mayer-Enthart et al., "Helical self-assembled chromophore clusters based on DNA-like architecture" Tetrahedron 63 (2007) 3434-3439.

McGraw et al., "A male-specific repeated DNA sequence in the domestic pig" Nucleic Acids Research, vol. 16, pp. 10389; 1988.

Nakamura et al., "Pyrene aromatic arrays on RNA duplexes as helical templates" Org. Biomol. Chem., 2007, 5, 1945-1951.

NCBI X12696—Sequence listing downloaded from http://www..ncbi.nlm.nih.gov/nuccore/2106; retrieved May 2, 2009.

Oeda et al., "Microwave-Assisted Synthesis of 2'-O-Aryluridine Derivatives" Organic Letters 2009 vol. 11, No. 24 5582-5585.

Ostergaard et al., "Novel insights into the use of Glowing LNA as nucleic acid detection probes—Influence of labeling density and nucleobases" Bioorganic & Medicinal Chemistry Letters 20 (2010) 7265-7268.

(56) References Cited

OTHER PUBLICATIONS

Pellestor, F. et al., "The Peptide Nucleic Acids: A New Way for Chromosomal Investigation on Isolated Cells?" Human Reproduction (2004) 19:9:1946-1951.
Perez-Lezaun et al., "Population Genetics of Y-Chromosome Short Tandem Repeats in Humans" J Mol. Evol, vol. 45, pp. 265-270, 1997.
Perret, J. et al., "A Polymorphic Satellite Sequence Maps to the Pericentric Region of the Bovine Y Chromosome," Genomics (1990) 6:3:482-490.
Rufer et al., "Telomere length dynamics in human lymphocyte subpopulations measured by flow cytometry" Nature Biotechnology; vol. 16, pp. 743-747; 1998.
Sakamoto et al., "Solid-phase detection of RNA using bispyrene-modified RNA probe" Nucleic Acids Symposium Series No. 50, 2006, 215-216.
Sakamoto et al., "Microarray-based label-free detection of RNA using bispyrene-modified 20-O-methyl oligoribonucleotide as capture and detection probe" Bioorganic & Medicinal Chemistry Letters 18 (2008) 2590-2593.
Sau at al. 'Invader LNA Efficient Targeting of Short Double Stranded DNA' Org Biomol Chem. 8(9): pp. 2028-2036. May 2010.
Sekine et al., "Synthesis and hybridization properties of 2'-O-methylated oligoribonucleotides incorporating 2'-O-naphthyluridines" Org. Biomol. Chem., 2011, 9, 210-218.
Tatusova, T. et al., "Blast 2 Sequences—A New Tool for Comparing Protein and Nucelotide Sequences" (1999) FEMS Microbiol. Let. 174:247-250.
Yamana et al., "2'-Pyrene modified oligonucleotide provides a highly sensitive fluorescent probe of RNA" Nucleic Acids Research, 1999, vol. 27, No. 11 2387-2392.
Yamana et al., "Synthesis of Oligonucleotide Derivatives With Pyrene Group at Sugar Fragment" Tetrahedron Letters, vol. 32, No. 44, pp. 6347-6350, 1991.
Yoshioka, K. et al., "Production of Piglets Derived From In-Vitro Produced Blastocysts Fertilized & Cultured in Chemically Defined Media: Effects of Theophylline, Adenosine, and Cysteine During In-Vitro Fertilization" Biology of Reproduction (2003) 69: 2092-2099.
European Patent Office Search Report for application No. 08861734.5 dated Dec. 30, 2010; (pp. 1-7).
United States Patent Office Action for U.S. Appl. No. 12/747,988 dated Apr. 5, 2013 (7 pages).
PCT/US2012/020139 International Search Report and Written Opinion dated Apr. 4, 2013 (15 pages).
PCT/US2008/086833 International Preliminary Report on Patentability dated May 21, 2009 (8 pages).
Fonvielle et al., "Decoding the Logic of the tRNA Regiospecificity of Nonribosomal FetnX$_{Wv}$ Aminoacyl Transferase", Cutting Edge Organic Chemistry, Angewandte Chemie International Edition, vol. 49, Issue 30, Jul. 12, 2010, pp. 5115-5119.
Gupta et al., "Synthesis and Biophysical Studies of Coronene Functionalized 2'-Amino-LNA: A Novel Class of Fluorescent Nucleic Acids", Bioconjugate Chem., 2010, 21, pp. 513-520.
Hrdlicka et al., "Targeting of mixed sequence double-stranded DNA using pyrene-functionalized 2'-amino-α-L-LNA," Chemical Communications, 2005, pp. 4279-4281.
Kalra et al., "Conformationally controlled high-affinity targeting of RNA or DNA by novel 2'-amino-DNA/LNA mixmers and pyrenyl-functionalized 2'-amino-DNA", Org. Biomol. Chem., 2004, 2, pp. 2885-2887.
Kumar et al., "2'-N-(Pyren-1-yl)acetyl-2'-Amino-α-L-LNA: Synthesis and Detection of Single Nucleotide Mismatches in DNA and RNA Targets", Chem Bio Chem, 2007, 8, pp. 1122-1125.
Kumar et al., "Functionalized 2'-Amino-α-L-LNA: Directed Positioning of Intercalators for DNA Targeting", J. Org. Chem., 2009, 74, pp. 1070-1081.
Kumar et al., "Nucleic Acid Structural Engineering Using Pyrene-Functionalized 2'-Amino-α-L-LNA Monomers and Abasic Sites", J. Org. Chem., 2008, 73, pp. 7060-7066.
Kumar et al., "Synthesis and Biophysical Studies of N2'-Functionalized 2'-Amino-α-L-LNA", Nucleosides, Nucleotides, and Nucleic Acids, 2007, 26, pp. 1403-1405.
Mahara et al., "Detection of Acceptor Sites for Antisense Oligonucleotides on Native Folded RNA by Fluorescence Spectroscopy", Bioorg. Med. Chem., 2003, 11, pp. 2783-2790.
Mahara et al. "Detection of acceptor sites for antisense olignucleotides on native folded RNA by fluorescence-labeled oligonucleotide", Nucleic Acids Research Supplement No. 3, 2003, pp. 7374.
Nakamura et al., "Pyrene aromatic arrays on RNA duplexes as helical templates", Org. Biomol. Chem., 2007, 5, pp. 1945-1951.
Ostergaard et al., "Novel insights into the use of Glowing LNA as nucleic acid detection probes—Influence of labeling density and nucleobases", Bioorg. Med. Chem. Lett., 2010, 20, pp. 7265-7268.
Sakamoto et al., "Solid-phase detection of RNA using bispyrene-modified RNA probe", Nucleic Acids Symposium Series No. 50, 2006, pp. 215-216.
Sekine et al. "Synthesis and hybridization properties of 2'-O-methylated oligoribonucleotides incorporating 2'-O-naphthyluridines", Org. Biomol. Chem., 2011, 9, pp. 210-218.
Umemoto et al., "Sensitive SNP Dual-Probe Assays Based on Pyrene-Functionalized 2'-Amino-LNA: Lessons to be Learned," ChemBioChem, vol. 8, 2007, pp. 2240-2248.
Veedu et al., "Locked Nucleic Acid as a Novel Class of Therapeutic Agents," RNA Biology, vol. 6., No. 3, Jul./Aug. 2009, pp. 321-323.
Yamana et al., "2'-Pyrene modified oligonucleotide provides a highly sensitive fluorescent probe of RNA", Nucleic Acids Research, 1999, vol. 27, No. 11, pp. 2387-2392.
GenBank, CT030234 (retrieved from http://www.ncbi.nlm.nih.gov/nuccore/89145300 on Oct. 7, 2012), Mar. 2, 2006.
International Search Report dated May 26, 2011, from International Application No. PCT/US2010/048520.
International Search Report dated Jan. 25, 2013, from International Application No. PCT/US2012/047442.
Written Opinion dated Jan. 25, 2013, from International Application No. PCT/US2012/047442.

* cited by examiner

GENDER-SPECIFIC SEPARATION OF SPERM CELLS AND EMBRYOS

CROSS-REFERENCE TO RELATED APPLICATIONS

This application is a national stage filing under 35 U.S.C. 371 of International Application No. PCT/US2008/086833, filed Dec. 15, 2008, which claims the benefit of priority to U.S. Provisional Patent Application No. 60/013,901, filed Dec. 14, 2007, the entire disclosure of which is herein incorporated by reference for any purpose.

INTRODUCTION

The production of offspring of a predetermined sex, or in a predetermined sex ratio, is desirable in a number of industries, including animal husbandry. The gender-specific separation of sperm cells or embryos may facilitate the production of offspring having a predetermined sex. Separated sperm cells may be used in artificial insemination or in vitro fertilization to produce zygotes that develop into organisms of a predetermined sex. However, techniques to produce populations of sperm cells or embryos that are sufficiently gender enriched are lacking.

SUMMARY

In one aspect, the invention provides a method for separating a population of sperm cells by contacting the population with a labeled oligonucleotide moiety capable of binding a gender-specific tandem repeat sequence that occurs in a portion of the population. The labeled sperm cells are then separated from the unlabeled sperm cells.

In another aspect, the invention provides a sperm cell or embryo having a gender-specific tandem repeat sequence and a labeled oligonucleotide moiety, such as a triplex forming oligonucleotide or a peptide nucleic acid, bound to the gender-specific sequence.

In another aspect, the invention provides a population of sperm cells or embryos having a gender-specific tandem repeat sequence occurring on the X or the Y chromosome, and a portion of the cells having a labeled oligonucleotide moiety, such as a triplex forming oligonucleotide or a peptide nucleic acid, bound to the gender-specific sequence.

BRIEF DESCRIPTION OF THE DRAWINGS

FIG. 2 includes histograms of boar sperm cells with CY3-labeled TFO (Sequence C) targeting the porcine Y chromosome GSTRS of SEQ ID NO: 1.

DETAILED DESCRIPTION

The invention relates to the generation of sperm cell fractions or embryos that are enriched for the X or the Y chromosome. In one embodiment, the invention provides methods for separating sperm cells that contain a labeled oligonucleotide moiety bound to a gender-specific tandem repeat sequence or a complement of a gender-specific tandem repeat sequence. The oligonucleotide moieties suitably bind in sufficient numbers to a region of the chromosome to generate a detectable signal that can be used as a basis for distinguishing and separating cells that contain the gender-specific tandem repeat sequence from those that do not. The invention further provides a method for the separation of sperm cells carrying an X chromosome from sperm cells carrying a Y chromosome. The gender-enriched sperm cell fractions can be used to fertilize ova to produce offspring of a predetermined sex. The invention further provides a method for selection of embryos carrying an X chromosome or embryos carrying a Y chromosome.

Figure 1:
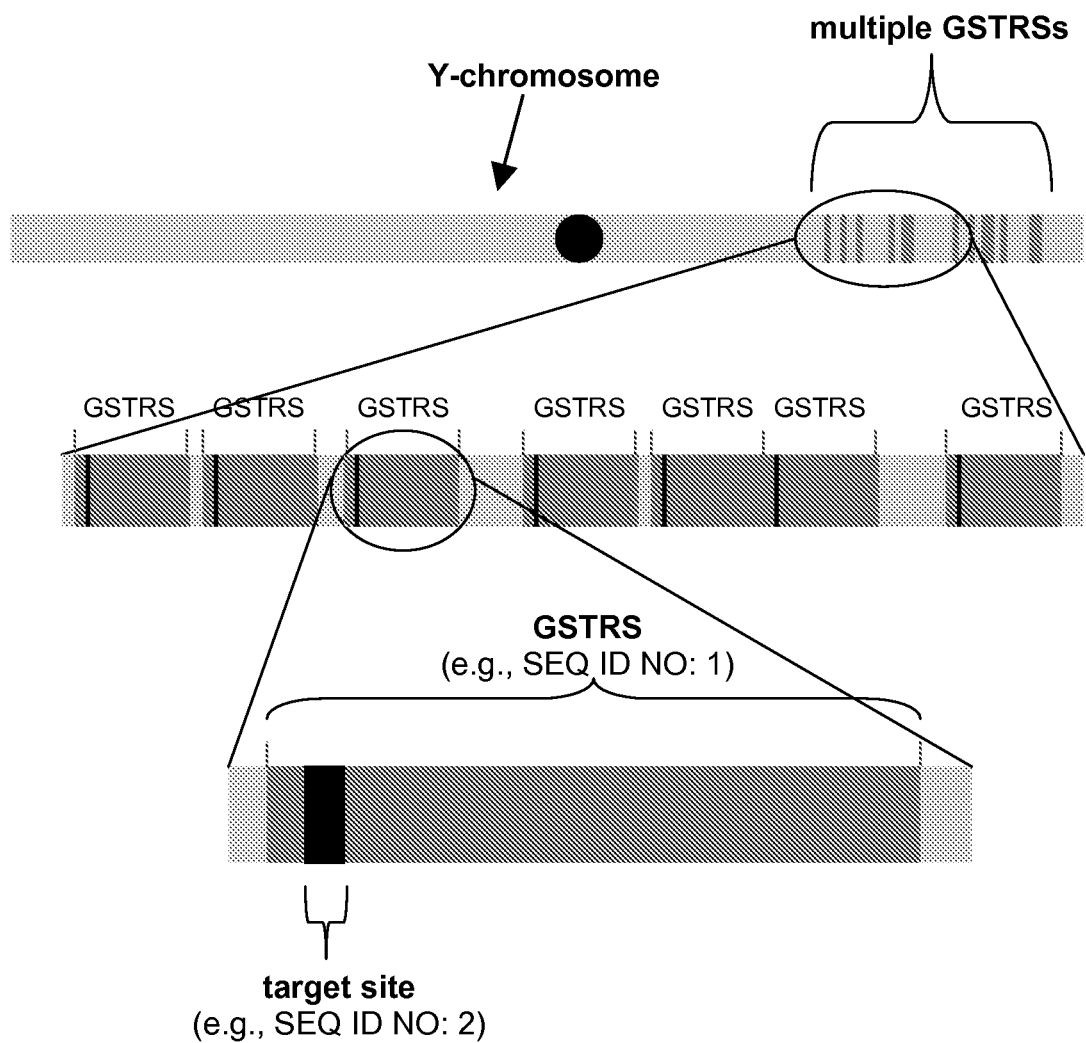
FIG. 1 is a schematic representation showing the location of gender-specific tandem repeat sequences (GSTRSs) and target sequences on a chromosome.

As used herein, a "gender-specific tandem repeat sequence," or "GSTRS" is a non-autosomal chromosome sequence that is repeated on either the Y chromosome or the X chromosome, but not both. Multiple GSTRSs occur in a region of the X or Y chromosome, as shown schematically in FIG. 1. The GSTRS may occur anywhere on the X or Y chromosome. In some embodiments, the GSTRS targets of the invention occur at or near the termini of the chromosome. The gender-specific tandem repeat sequence may comprise at least about 50 nucleotides, at least about 100 nucleotides, at least about 500 nucleotides, at least about 1,000 nucleotides, at least about 2,000 nucleotides, at least about 3,000 nucleotides, or at least about 4,000 nucleotides, and less than about 10,000 nucleotides, less than about 9,000 nucleotides, less than about 8,000 nucleotides, less than about 7,000 nucleotides, less than about 6,000 nucleotides, or less than about 5,000 nucleotides. Suitably there are less than about 50,000 nucleotides, about 10,000 nucleotides, about 5,000 nucleotides, about 3,000 nucleotides, about 2,000 nucleotides, about 1,000 nucleotides, about 500 nucleotides, about 300 nucleotides, about 100 nucleotides, about 10 nucleotides, about 1 nucleotide, or zero nucleotides between each unit of the repeated GSTRS. The GSTRS does not have to be repeated as exactly the same sequence, and some variation in the repeated sequences is possible without effecting the scope of the invention. The units of repeated GSTRSs may share at least about 70%, at least about 80%, at least about 85%, at least about 90%, at least about 95%, at least about 97%, at least about 98%, or at least about 99% identity with each other. Percent identity may be determined using algorithms used in BLASTn or MEGABLAST programs, which may be used to obtain sequences homologous to a reference polynucleotide, as is known in the art. Algorithms used for sequence alignment are described by Tatiana A. Tatusova, Thomas L. Madden (1999), FEMS Microbiol Lett. 174:247-250. The GSTRS may be repeated at least about 50 times, at least about 100 times, at least about 200 times, at least about 300 times, at least about 400 times, at least about 500 times, at least about 750 times, or at least about 1000 times on a chromosome.

For each GSTRS, an oligonucleotide moiety may be selected to bind to the GSTRS or a complement of the GSTRS. As depicted schematically in FIG. 1, the oligonucleotide moiety may target a shorter target sequence within the GSTRS. As used herein, "target sequence" is a segment of DNA within the GSTRS, wherein the oligonucleotide moiety binds the target sequence or the complement of the target sequence. The target sequence may include at least about 4, at least about 6, at least about 8, at least about 10, at least about 12, or at least about 14 nucleotides. The target sequence may include less than about 100, less than about 90, less than about 80, less than about 70, less than about 50, less than about 40, less than about 30, less than about 20, or less than about 16 nucleotides. The oligonucleotide moiety may bind to at least about 4 nucleotides, at least about 5 nucleotides, at least about 6 nucleotides, at least about 9 nucleotides, at least about 12 nucleotides, at least about 15 nucleotides, at least about 20 nucleotides, at least about 25 nucleotides, at least about 30 nucleotides, or at least about 35 nucleotides of the GSTRS or the complement of the GSTRS. The oligonucleotide moiety may bind to less than about 100 nucleotides, less than about 50 nucleotides, less than about 45 nucleotides, less than about 40 nucleotides, or less than about 20 nucleotides of the GSTRS or the complement of the GSTRS.

Suitable GSTRSs may be selected by searching public databases for DNA sequences that are highly repetitive on only the X or the Y chromosome. Suitable target sequences within the GSTRS may be selected by scanning the GSTRS for consecutive purines or consecutive pyrimidines, for example, homopurine or homopyrimidine sequences. Homopurine or homopyrimidine sequences facilitate binding of oligonucleotide moieties such as triplex-forming oligonucleotides (TFOs) to the major groove of duplex DNA to form a triplex. The target sequence within the gender-specific tandem repeat sequence may include, but is not limited to, homopurine or homopyrimidine sequences, as in certain embodiments, oligonucleotide moieties are capable of binding DNA of any sequence.

In some embodiments, the target sequence is itself a repeated unit within the GSTRS. The GSTRS may include at least about 1, at least about 2, at least about 3, at least about 4, at least about 5, at least about 7, at least about 10, at least about 15, at least about 50, at least about 100, or at least about 200 repeated units of target sequence. A GSTRS having a higher number of repeated units will facilitate binding of more oligonucleotide moieties to the GSTRSs. Suitably, at least about 5, at least about 10, at least about 100, at least about 200, at least about 300, at least about 400, at least about 500, at least about 1,000, at least about 5,000, at least about 25,000, or at least about 50,000 oligonucleotide moieties bind to the GSTRSs.

In some embodiments, more than one target sequence may be selected within the GSTRS, or a complement of the GSTRS. A GSTRS having a higher number of target sequences will facilitate binding of more oligonucleotide moieties to the GSTRSs. In other embodiments, more than one type of oligonucleotide moiety may be selected to bind the GSTRS or a complement of the GSTRS.

The oligonucleotide moiety that binds to the target sequence is a peptide nucleic acid (PNA) or a triplex forming oligonucleotide (TFO).

A PNA is two or more purine or pyrimidine bases linked to a peptide backbone. The PNA backbone is made of repeating N-(1-aminoethyl)-glycine units linked by peptide bonds, with the bases linked to the backbone by methylene carbonyl bonds. The neutral backbone of PNAs facilitates binding DNA with reduced charge repulsion relative to the phosphodiester backbone. PNAs bind duplex DNA by forming Watson-Crick pairs with the target sequence or complement of the target sequence, and creating a single-stranded DNA loop. PNAs and methods for generating PNAs are described in U.S. Pat. No. 5,539,082 and Pellestor et al. (*Human Reproduction* (2004) volume 19, pages 1946-1951), which are incorporated herein by reference in their entireties. In some embodiments, the PNA includes a detectable label attached to the sequence by an ester or other linkage, as further described below.

A TFO is a sequence of at least two nucleotides capable of binding within the major groove of a DNA double helix in a sequence-specific manner. A TFO binds to DNA bases and/or RNA bases to form a triple helical structure. For example, a TFO may target a homopurine or homopyrimidine sequence in the DNA double helix to form a triple helix. Purine TFOs and pyrimidine TFOs each bind purine sequences. Purine TFOs bind in the major groove of duplex DNA using reverse Hoogsteen hydrogen bonds and run antiparallel to the purine sequence. Pyrimidine TFOs bind in the major groove of duplex DNA using Hoogsteen hydrogen bonds and run parallel to the purine sequence (see Li, J. et al. (2003) *Journal of the American Chemical Society* volume 125, pages 2084-2093, which is incorporated herein by reference in its entirety). Suitable TFOs and methods of generating TFOs are described in U.S. Pat. Nos. 5,176,996 and 5,962,426, which are incorporated herein by reference in their entireties. TFOs may be synthesized by standard phosphoramidite synthesis or other techniques known in the art.

OligoTRIPs are a type of synthetic TFO that recognize and bind the major groove of a DNA duplex of any sequence and do not require homopurine or homopyrimidine target sequences. OligoTRIPs can target a sequence comprising both purines and pyrimidines because the glycosidic bond of the OligoTRIP backbone is near the center of the major groove and perpendicular to the Watson-Crick hydrogen bonds of the target duplex DNA. The location of the glycosidic bond and the capacity of OligoTRIP bases to recognize A:T versus T:A and C:G versus G:C allow the OligoTRIP bases to bind purines on either side of the major groove of the duplex DNA. OligoTRIPs may be synthesized from one or more heterocyclic OligoTRIP monomers, such as AntiAT-F, AntiTA, AntiGC, or AntiCG. Suitable OligoTRIPs and methods of generating OligoTRIPs are described in U.S. Pat. No. 5,844,110 and U.S. Patent Application Publication No. US 2006/0281907, which are incorporated herein by reference in their entireties. OligoTRIPs incorporate a quinazoline or quinoline base moiety, such as 2-amino-6-fluoro-quinoline or 2-amino-quinazoline. In contrast, non-OligoTRIP TFOs, herein referred to as "naturally occurring TFOs," have purine or pyrimidine base moieties (for example A, C, T or G) such as are found in naturally occurring polynucleotides. The sugar or base moieties of naturally occurring TFOs may be modified, for example by methylation, to enhance their capacity to bind target sequences. Suitably, an internal cytosine may be methylated as 5-methyl cytosine.

The oligonucleotide moiety that binds to the GSTRS may include a label that is detectable when bound to the gender-specific tandem repeat sequence. Suitable labels include, but are not limited to, dyes, fluorescent molecules such as CY3 or CY5, molecules of heavy density such as gold or iron, magnetic molecules, nanoparticles, picoparticles, or any combination thereof. The labeled oligonucleotide moiety binds in sufficient numbers to the GSTRSs to produce a detectable signal. The signal may be detectable by any suitable method including, but not limited to, centrifugation, fluorescence, luminescence, microscopy, magnetic force, densitometry, or combinations thereof. Methods of coupling labels to oligonucleotides are known in the art and can be adapted for coupling to the oligonucleotide moieties described herein.

In other embodiments, oligonucleotide moieties may be labeled with labels that are active for fluorescence resonance energy transfer (FRET). Some oligonucleotide moieties may be labeled with a FRET donor, and others may be labeled with a FRET acceptor. Excitation of the donor label may excite the acceptor label, and cause the acceptor label to fluoresce. FRET may thus be used to enhance or differentiate the signal of the labeled oligonucleotide moieties bound to GSTRSs in proximity on the chromosome and improve signal to noise ratio. For example, two oligonucleotide moieties can be designed to bind to a target sequence so that the oligonucleotide moieties are located close to each other after binding to the target sequence, e.g., a first oligonucleotide moiety may be designed to bind base pairs 1 to 12 and a second oligonucleotide moiety may be designed to bind base pairs 13 to 24 of a target sequence 24 base pairs in length. When the two different oligonucleotide moieties are labeled with suitable dye molecules, for example a cyan fluorescent protein (CFP) as donor and yellow fluorescent protein (YFP) as acceptor, FRET may be used. The labeled cells may be excited with light of a suitable wavelength. For example, if excited with a wavelength of 440 nm, CFP will emit light at 480 nm wavelength which overlaps with the excitation wavelength of YFP, and will lead to a YPF signal emission peak at 535 nm when both oligonucleotide moieties are close together.

In another embodiment, the label may suitably be a molecule or atom attached to the oligonucleotide moiety that enhances activation or deactivates physiological process of the cell, and may be toxic and/or facilitates destruction, incapacitation or inactivation of the cell when bound to a GSTRS. For example, a cell toxin when attached to the GSTRS, may cause the cell to die, may facilitate impairment of the functioning of the cell, may disrupt the cell physiologically, or may impair cellular integrity, so that the cell becomes unviable or incapacitated. Mechanisms through which the label may affect the cell include, without limitation, increase intra-cellular pH, accumulation of cell toxins, induction of selective phototoxicity, cell death through the action of electromagnetic waves on the label and combinations thereof. The Enriched sperm cell fractions may be thus be generated without needing to separate a viable population of labeled cells from a viable population of unlabeled cells. Such a label may be used in conjunction with, or independently from, one or more detectable labels bound to the same or other oligonucleotide moieties.

Suitably, the molecule or atom that facilitates destruction or incapacitation of the cell functions effectively when in proximity to other labels, which labels may be the same or different, and which may each be attached to separate oligonucleotide moieties, as would occur upon binding of the oligonucleotide moiety to the GSTRS.

Labels may also be used which regulate the capacitation of sperm cells containing a GSTRS. Accordingly, the timing at which a labeled sperm cell containing the GSTRS has the capacity to fertilize an egg may be controlled. For example, a sperm cell may be incapacitated in its ability to fertilize an oocyte, by inducing premature capacitation. Fertilization of an egg can then be delayed by an appropriate amount of time, such that the labeled fraction of cells in the population are unable to fertilize the egg.

Suitable labels which may be used include, for example, noble metals such as silver, gold, platinum, palladium, rhodium, and iridium, and alloys and molecules thereof, as well as magnetic compounds. Suitably these labels may be attached as pico particles or nanoparticles. Cells labeled with such metals or compounds may subsequently be exposed to electromagnetic radiation, such as radiowaves, which may heat and/or excite the label resulting in the viability of the cell being impaired or reduced. Other suitable labels include calcium or calcium-containing compounds, calcium/ion pump activators, hydrogen ion/pH pump activators, organic compounds with alcohol groups, acids, and denaturing enzymes such as trypsin.

Labels may be attached to oligonucleotides using techniques known in the art for generally coupling molecules to oligonucleotides.

In a further embodiment, methods for distinguishing and separating sperm cells or embryos that contain an oligonucleotide moiety bound to a GSTRS. In some embodiments, the sperm cells or embryos are mammalian. Suitably, the sperm cells or embryos are mammalian, piscian or avian, or from vertebrates. The sperm cells may be of porcine, equine, bovine, ovine, caprine, feline, canine, or human origin. In other embodiments, the sperm cells or embryos are piscian or avian. As used herein, a "population" of sperm cells or embryos means at least two sperm cells or two embryos.

In a first step of the method to generate gender-enriched sperm cell fractions, sperm cells are contacted with the labeled oligonucleotide moiety. In some embodiments, the sperm cell is permeabilized to facilitate entry of the oligonucleotide into the sperm cells and access to the GSTRS. The sperm cells may be permeabilized by any suitable technique, including but not limited to, osmotic pressure, electroporation, liposomes, permeating peptides, a modified (for example increased or decreased) temperature or combinations thereof. In other embodiments, the labeled oligonucleotide moiety is passively or actively transported into the cell. The oligonucleotide moiety may further include a transport moiety, such as a transport peptide, that facilitates or mediates active uptake of the oligonucleotide moiety into the sperm cell. Suitable transport peptides are commercially available from AnaSpec (San Jose, Calif., U.S.A.) and include Arg9, TAT, and Cys-TAT. Transport peptides compatible with the ergothioneine transporter may also be used.

Once the oligonucleotides are bound to the repeated DNA sequence, the sperm cells may be separated. The clustering of the labeled oligonucleotide moiety in the region of the GSTRS produces a signal that is detectable and enables cells that contain the GSTRS to be distinguished from cells that do not contain the GSTRS. Once labeled, the sperm cells may be detected and separated. Suitable methods for separating sperm cells include, but are not limited to, centrifugation, magnetic force, flow cytometry, densitometry, or any combination thereof. Suitably, at least about 25%, at least about 30%, at least about 40%, at least about 50%, at least about 60%, at least about 70%, at least about 80%, at least about 90%, or at least about 95% of the cells in the separated population of sperm cells comprise a labeled oligonucleotide moiety bound to the GSTRS. The population of sperm cells may be separated into a labeled fraction that contains the GSTRS, and an unlabeled fraction that does not contain the GSTRS.

In one embodiment, the labeled fraction includes sperm cells containing an X chromosome labeled with the oligonucleotide, and the unlabeled fraction includes sperm cells containing Y chromosome not labeled with oligonucleotide. In another embodiment, the labeled fraction includes sperm cells containing a Y chromosome labeled with the oligonucleotide, and the unlabeled fraction includes sperm cells containing an X chromosome not labeled with oligonucleotide. Suitably, a fraction may contain sperm cells wherein at least about 60%, at least about 65%, at least about 70%, at least about 75%, at least about 80%, at least about 85%, at least about 90%, at least about 95%, or at least about 99% of the sperm cells comprise an X chromosome. Alternatively, a fraction may contain sperm cells wherein at least about 60%, at least about 65%, at least about 70%, at least about 75%, at least about 80%, at least about 85%, at least about 90%, at least about 95%, or at least about 99% of the sperm cells comprise a Y chromosome.

The separated fractions suitably contain viable sperm cells. As used herein, "viable" refers to a sperm cell that is able to fertilize an egg to produce an embryo. Suitably, a separated sperm fraction contains sperm wherein at least about 20%, at least about 30%, at least about 40%, at least about 50%, at least about 60%, at least about 70%, at least about 80%, at least about 90%, at least about 95%, or at least about 99% of the sperm cells are viable.

A gender-enriched sperm cell fraction may be used to fertilize an egg in vitro or in vivo. Fertilization of an egg may be accomplished, for example, via artificial insemination, including, but not limited to, intra-vaginal, intra-cervical, intra-uterine or surgical insemination, or by intracytoplasmic sperm injection (ICSI). A labeled fraction or unlabeled fraction may be used for in vivo or in vitro fertilization. The fertilized egg may be allowed to develop to produce an embryo of predetermined sex.

In a further embodiment, the invention provides methods for determining the sex of embryos. Labeled oligonucleotide moieties designed to bind to a GSTRS as described above may be incubated with embryos, enter the embryos, and bind the GSTRS. As with sperm cells, the embryos may be permeabilized to facilitate entry of the labeled oligonucleotide moiety into the embryos. One or more cells from the embryo may also be removed or biopsied and permeabilized to facilitate entry of the labeled oligonucleotide. The sex of the biopsied cells may then be correlated with the embryo from which the cells were removed. Once the oligonucleotide moiety is bound to the GSTRS, the embryos may be viewed under a dissecting microscope or fluorescent microscope to distinguish embryos that contain the GSTRS from those that do not contain the GSTRS. As with sperm cells as described above, the population of embryos may be separated into a labeled fraction that contains the GSTRS, and an unlabeled fraction that does not contain the GSTRS.

The following examples are provided to assist in a further understanding of the invention. The particular materials and conditions employed are intended to be further illustrative of the invention and are not limiting upon the reasonable scope of the appended claims.

EXAMPLES

Example 1: Porcine GSTRSs, Target Sequences, and Corresponding Oligonucleotide Moieties Two PNAs designated "Sequence A" and "Sequence B" each bind the target sequence shown in SEQ ID NO: 2. SEQ ID NO: 2 is a 16-nucleotide sequence at nucleotide positions 344 to 359 of the GSTRS depicted in SEQ ID NO: 1. SEQ ID NO: 1 occurs on the porcine Y chromosome and has sequence Accession number X12696 (McGraw et al. (1988) *Nucleic Acids Research*, volume 16, page 10389). PNAs may be designed to bind to a specific sequence using materials and information commercially available from Applied Biosystems. Sequence A and Sequence B were each custom synthesized with a CY3 fluorescent molecule attached to the 5'-end by an ester bond. Sequences A and B were custom-ordered from Bio-Synthesis, Inc. (Lewisville, Tex., U.S.A.). PNAs were received as a lyophilized powder, and they were resuspended in ultrapure water and stored in aliquots at −20° C. and at −80° C.

A TFO designated "Sequence C", which binds the target sequence shown in SEQ ID NO: 2, was custom synthesized with a CY3 fluorescent molecule linked to the 5'-end by an ester bond. A TFO designated "Sequence D" was designed to bind to the target sequence shown in SEQ ID NO: 3 and was custom synthesized with a CY3 fluorescent molecule linked to the 5'-end by an ester bond. SEQ ID NO: 3 is a 20-nucleotide sequence at nucleotide positions 3681 to 3700 of the GSTRS shown in SEQ ID NO: 1.

A 205 base pair GSTRS was identified on the porcine X chromosome at locus AY574041 (SEQ ID NO: 4). Two TFOs designated "Sequence H" and "Sequence I" were designed to bind to the target sequence shown in SEQ ID NO: 9. SEQ ID NO: 9 is a 15-nucleotide sequence at the 3'-end of the GSTRS shown in SEQ ID NO: 4. Sequence H was custom synthesized with a FAM fluorescent molecule linked to the 3'-end, and Sequence I was custom synthesized with a CY3 fluorescent molecule linked to the 5'-end by an ester bond. A PNA designated "Sequence J" was designed to bind to the target sequence shown in SEQ ID NO: 9, and includes a "J base" moiety: 2'-Deoxypseudoisocytidine CEP (ψ-iso-dC). Sequence J was custom synthesized with a BoDIPY FLX (FITC-like) fluorescent molecule linked to the 5'-end by a linker.

A 1399 base pair GSTRS was identified on the bovine X chromosome at locus V00125 (SEQ ID NO: 5) with sequence Accession number V00125. A TFO designated "Sequence E" was designed to bind to the target sequence shown in SEQ ID NO: 6. SEQ ID NO: 6 is a 16-nucleotide sequence at nucleotide positions 1157 to 1172 of the GSTRS shown in SEQ ID NO: 5. Sequence E was custom synthesized with a CY3 fluorescent molecule linked to the 5'-end by an ester bond.

A somatic tandem repeated DNA sequences was identified on porcine chromosome 1 with sequence Accession number X51555 (SEQ ID NO: 7). It is a 313 base pair DNA sequence that is repeated approximately 3000 to 6000 times. Two TFOs designated "Sequence F" and "Sequence G" were each designed to bind to the target sequence shown in SEQ ID NO: 8. SEQ ID NO: 8 is a 14-nucleotide sequence at nucleotide positions 120 to 133 of the tandem repeat DNA sequence shown in SEQ ID NO: 7. Both Sequence F and Sequence G were each custom synthesized with a CY3 fluorescent molecule linked to the 5'-end by an ester bond. This somatic DNA sequence (SEQ ID NO: 7) was used as a negative control for experiments.

Examples of DNA sequences of porcine GSTRSs, target sequences, and corresponding oligonucleotides moieties are shown in Table 1 below.

TABLE 1

| Name | Description | DNA Sequence, 5' → 3' |
|---|---|---|
| SEQ ID NO: 1 | GSTRS on porcine Y chromosome. | See SEQ ID NO: 1. |
| SEQ ID NO: 2 | Target sequence near the 5'-end of the GSTRS shown in SEQ ID NO: 1. | 5'-GAGAGAGAGA GAGAGA-3' |
| SEQ ID NO: 3 | Target sequence near the 3'-end of the GSTRS shown in SEQ ID NO: 1. | 5'-TCTAGAGAAG GAGGAGGATT-3' |
| SEQ ID NO: 4 | GSTRS on porcine X chromosome. | See SEQ ID NO: 4. |
| SEQ ID NO: 5 | GSTRS on bovine X chromosome. | See SEQ ID NO: 5. |

TABLE 1-continued

| Name | Description | DNA Sequence, 5' → 3' |
|---|---|---|
| SEQ ID NO: 6 | Target sequence in the GSTRS shown in SEQ ID NO: 5. | 5'-AGGAGGGGAG AAAGGG-3' |
| SEQ ID NO: 7 | Tandem repeat sequence on porcine chromosome 1. | See SEQ ID NO: 7. |
| SEQ ID NO: 8 | Target sequence in the tandem repeat sequence shown in SEQ ID NO: 7. | 5'-TCCGCCTCCT CCCT-3' |
| SEQ ID NO: 9 | Target sequence at the 5'-end of the GSTRS shown in SEQ ID NO: 4. | 5'-CTCCCTTCTG TCTTT-3' |
| Sequence A SEQ ID NO: 12 | PNA; binds to target sequence shown in SEQ ID NO: 2. | 5'-TCTCTCTCTC TCTCTC-3' |
| Sequence B SEQ ID NO: 13 | PNA; binds to target sequence shown in SEQ ID NO: 2. | 5'-TCTCTCTCTC TC-3' |
| Sequence C SEQ ID NO: 14 | TFO; binds to target sequence shown in SEQ ID NO: 2. | 5'-CTCTCTCTCT CTCTCT-3' |
| Sequence D SEQ ID NO: 15 | TFO; binds to target sequence shown in SEQ ID NO: 3. | 5'-TCTCTTCCTCCTCCT-3' |
| Sequence E SEQ ID NO: 16 | TFO; binds to target sequence shown in SED ID NO: 6. | 5'-TCCTCCCCTC TTTC-3' |
| Sequence F SEQ ID NO: 17 | TFO; binds to target sequence shown in SEQ ID NO: 8. | 5'-TCCCTCCTCC TCCT-3' |
| Sequence G SEQ ID NO: 18 | TFO; binds to target sequence shown in SEQ ID NO: 8. | 5'-GGTGGTGGGT-3' |
| Sequence H | TFO; binds to target sequence shown in SEQ ID NO: 9. | 5'-GTGGGTTGT-3' |
| Sequence I | TFO; binds to target sequence shown in SEQ ID NO: 9. | 5'-GTGGGTTGT-3' |
| Sequence J SEQ ID NO: 19 | PNA; binds to target sequence shown in SEQ ID NO: 9. | 5'-CTCCCTTCTG TCTTTAT-3' |
| Sequence K SEQ ID NO: 20 | PNA; binds to target sequence shown in SEQ ID NO: 11. | 5'-AGC CCT GTG CCC TG-3' |

Example 2: Generation of a CY3-Labeled Triplex Forming Oligonucleotide (TFO) Conjugate Triplex forming oligonucleotides (TFOs) were obtained from Unimed Medical Center (University of Nebraska-Omaha, Omaha, Nebr., U.S.A.) or Integrated DNA Technologies (Coralville, Iowa, U.S.A.). A labeled CY3-TFO conjugate was made by linking a CY3 dye, commercially available from Applied Biosystems (Foster City, Calif., U.S.A.), to the 5'-end of the TFO prepared as described in Example 1 (designated Sequence C) with an ester linkage. The internal cytosines were methylated.

Example 3: Method of Labeling Fixed Boar Sperms Cells with CY3-PNA Conjugate

Freshly-ejaculated boar semen or thawed boar semen (about 100 million sperm cells) was added to 10 mL of phosphate-buffered saline (PBS). The suspension was centrifuged for 5 minutes at 800×g. The pellet was resuspended in 1 mL of 3 M NaOH. The suspension was incubated at room temperature for 5 minutes and centrifuged for 5 minutes at 800×g. The pellet was resuspended in 2 mL of PBS and centrifuged for 5 minutes at 800×g. The pellet was resuspended in PBS or phosphate buffer (PB) to obtain a final concentration of 10 million sperm cells per mL of PBS.

After pre-treatment of the sperm cells, CY3 labeled-PNA as prepared in Example 1 (designated Sequence A) was incubated with the sperm cells at a final PNA concentration of 50 ng/mL for 7 minutes at 75° C. The suspension was allowed to cool to room temperature and then incubated at room temperature for 45 minutes. Sperm cells were centrifuged for 5 minutes at 800×g, the pellet was resuspended in PBST (PBS with 0.05% Tween 20), and the suspension was incubated for 20 minutes at 45° C. The sperm cells were centrifuged for 5 minutes at 800×g, and the pellet was resuspended in PBS or PB. CY3 labeled (Sequence A)-PNA-treated sperm cells (4 μL) were viewed under a Zeiss AxioSkop fluorescence microscope. DAPI stain was optionally added to the sample just before observation with the microscope. Selective binding of the CY3 labeled-PNA to the Y chromosome of fixed boar semen was observed. Fixed boar sperm cells pretreated with NaOH and RNase A and incubated with Y-chromosome specific CY3-PNA Y90-1 stained Y chromosomes red. Somatic porcine chromosomes treated with Y-chromosome specific CY3-PNA Y90-1 were stained red. Somatic porcine chromosomes stained with DAPI that binds DNA and RNA and were stained blue. A merged image of somatic porcine chromosomes stained with DAPI and CY3-PNA Y90-1 was generated. Y-chromosomes appeared to be stained pink, indicating selective binding of CY3-PNA Y90-1 to the Y-chromosomes.

We found the signals present in 161 of 302 (53.3%) sperm to consist of a single, centrally-located, round fluorescent label in the sperm head.

As a control, freshly-ejaculated boar semen was prepared and permeabilized as described above. A CY3-PNA conjugate with base sequence (CCCTAA)$_3$, commercially available from Applied Biosystems (Foster City, Calif., U.S.A.) that binds to the telomeres of all mammalian chromosomes was incubated with the resuspended sperm cells in PBS at a final PNA concentration of 1 ng/μL for 1 to 18 hours at room temperature. CY3-PNA (CCCTAA)$_3$-treated sperm cells (4 μL) were viewed under a Zeiss AxioSkop fluorescence microscope. Selective binding of CY3-PNA (CCCTAA)$_3$ to all porcine chromosome telomeres of fixed boar semen was observed. Chromosomes stained with 4',6-diamidino-2-phenylindole (DAPI) that non-specifically binds DNA and RNA appeared blue. In contrast, CY3-PNA (CCCTAA)$_3$ stained chromosomes pink.

Example 4: Method of Labeling Fixed Boar Sperm Cells with CY3-TFO Conjugate

Freshly-ejaculated boar semen or thawed boar semen (about 100 million sperm cells) was added to 10 mL of PBS. The suspension was centrifuged for 5 minutes at 800×g, and the pellet was resuspended in 1 mL of 3 M NaOH. The suspension was incubated at room temperature for 5 minutes and centrifuged for 5 minutes at 800×g. The pellet was washed in 2 mL of PBS and centrifuged for 5 minutes at 800×g. The pellet was resuspended in PBS or PB to obtain a final concentration of 10 million sperm cells per mL of PBS.

Figure 2A:
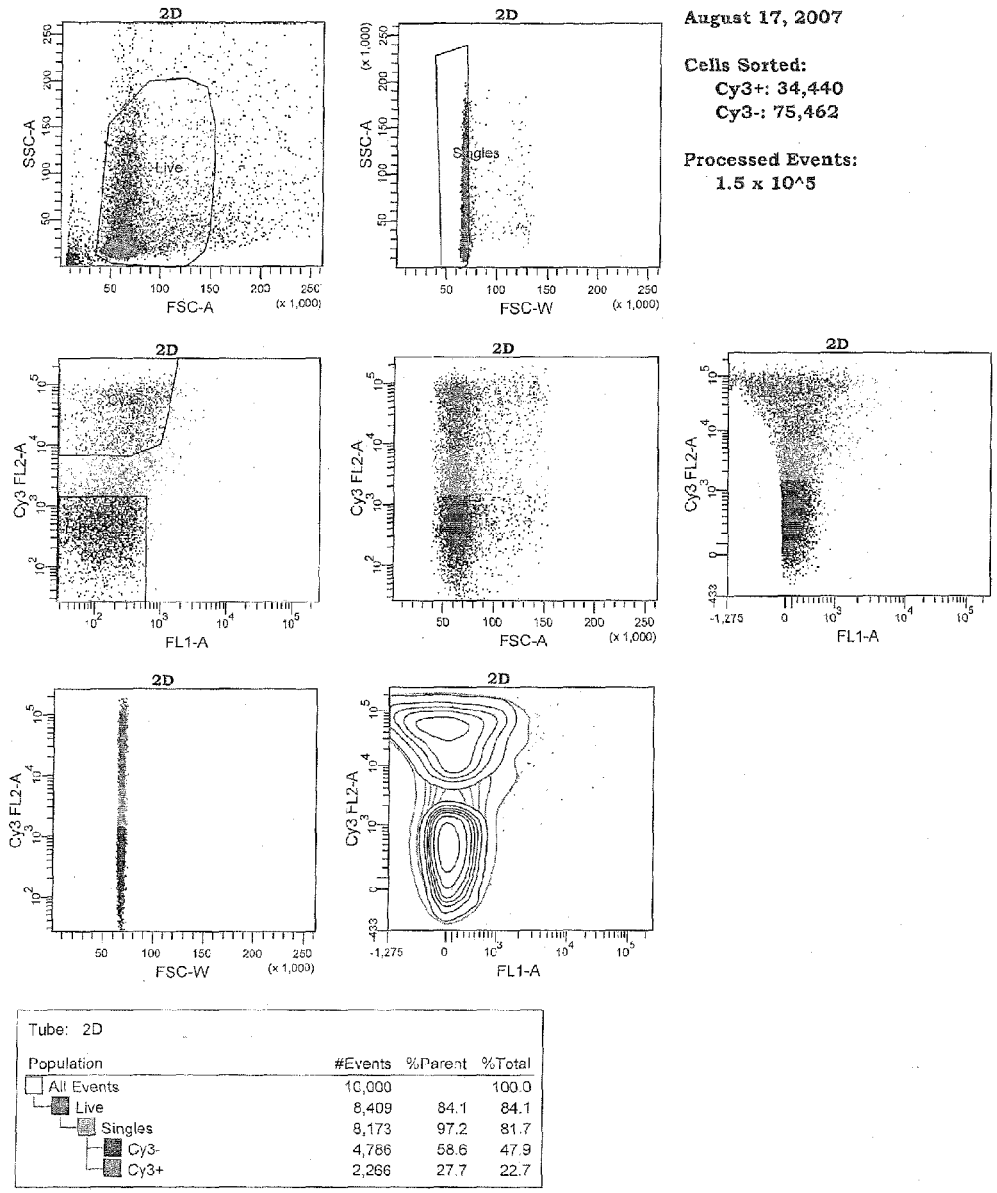
FIG. 2A depicts data from sorted samples with CY3-labeled TFO and FIG. 2B depicts data from the negative control.
Figure 2B:
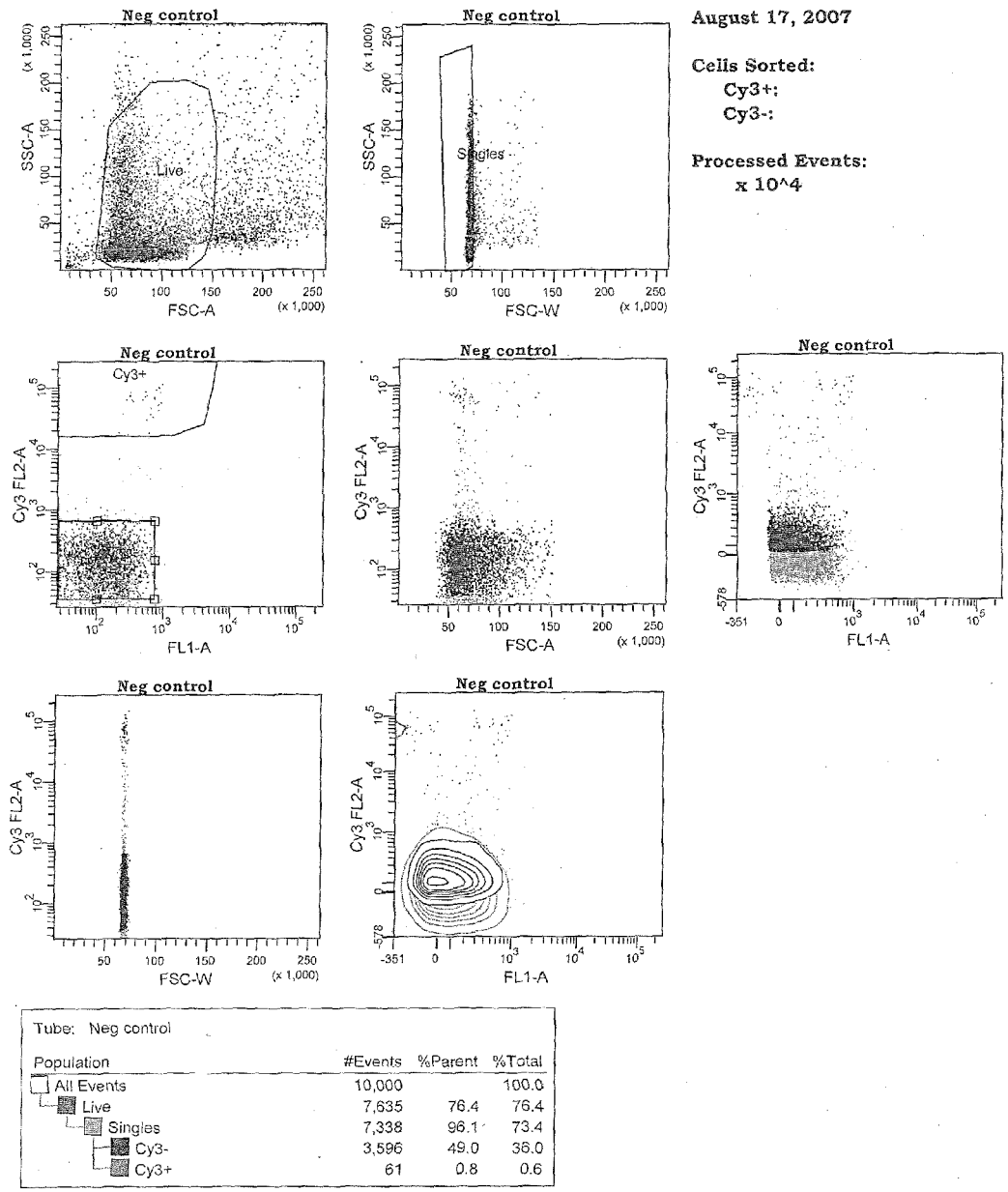

After pre-treatment of the sperm cells, 2 mM MgCl$_2$ was added to the sperm cell suspension. The suspension was incubated with the fluorescently labeled TFO conjugate at a final concentration of 50 ng/mL at 60 to 70° C. for 20 minutes to 1 hour. The suspension was centrifuged at room temperature at 800×g for 5 minutes, the supernatant was aspirated, and the pellet was resuspended in PBS or PB. CY3-TFO-treated sperm cells were viewed under a Zeiss AxioSkop fluorescence microscope to confirm that the chromosomes were labeled with CY3-TFO conjugate. Flow cytometry was used to analyze the semen. Histograms of boar sperm cells with CY3-labeled TFO (of Sequence C) targeting the porcine Y chromosome GSTRS of SEQ ID NO: 1 are shown in FIGS. 2A and 2B. FIG. 2A depicts flow data from sorted samples with CY3-labeled TFO and FIG. 2B depicts flow data from the negative control.

Example 5: Separation of Fluorescently Labeled Boar Sperm Cells Via Flow Cytometry Boar sperm cells were permeabilized by adding approximately 100 million sperm cells to 10 mL of PBS. The suspension was centrifuged for 5 minutes at 800×g, and the pellet was resuspended in 1 mL of 1 to 3 M NaOH. The suspension was incubated at room temperature for 5 minutes and centrifuged for 5 minutes at 800×g. The pellet was washed in 2 mL of PBS and centrifuged for 5 minutes at 800×g. The pellet was resuspended in PBS or PB to obtain a final concentration of 10 million sperm cells per mL of PBS. After pre-treatment of the sperm cells, 2 mM MgCl$_2$ was added to the sperm cell suspension. The suspension was incubated at 60 to 70° C. for 20 minutes to 1 hour.

A PNA as prepared in Example 1 (Sequence A; labeled with CY3) was incubated with the sperm cells at 1 ng/μL PNA for 1 to 18 hours at room temperature. Boar sperm cells were then separated using a FACSVantage SE with DiVa option flow cytometer (BD Biosciences, San Jose, Calif., U.S.A.) with 100 mW of 488 nm light from a Coherent INNOVO 90C Argon ion laser. A 100 μm nozzle tip was used at a sheath pressure of 12 psi. The sheath fluid used was sterile Dulbecco's Phosphate Buffered Saline (DPBS, without Ca$^{2+}$ or Mg$^{2+}$, Sigma-Aldrich, St. Louis, Mo., U.S.A.). Detectors used included FSC-A for forward scatter, SSC-A for side scatter, FL1-A with a 530/30 nm bandpass filter to detect any auto-fluorescent material, FSC-W for doublet-discrimination, and FL2-A CY3 detector with a 585/42 nm bandpass filter to detect the PNA with CY3 fluorescent label. A flow cytometry histogram illustrating the separation of labeled and unlabeled boar sperm cells demonstrated selective binding of CY3-PNA (Sequence A) to the Y chromosome and separation of sperm with X chromosome from sperm with Y chromosome. At least 85% of the cells in the labeled fraction are expected to contain the Y chromosome. At least 85% of the cells of the unlabeled fraction are expected to contain the X chromosome.

Example 6: Separation of Fluorescently Labeled Viable Sperm Cells Via Flow Cytometry Semen will be resuspended in semen extender (AndroHep CellGuard for boar sperm, commercially available from Minitube of America, Verona, Wis., U.S.A.) to give approximately 1×10$^7$ cells per mL. 1 ng of CY3-PNA conjugate of Example 1 (Sequence A) will be added to 0.6 mL of sperm cell suspension. The suspension will be placed into a 0.4 cM electrode Bio-Rad cuvette (Bio-Rad, Hercules, Calif., U.S.A.), and the cells will be permeated using a pulsive Gene Pulser (Bio-Rad) set to 400 volts at 25 uFD capacitance after 5 seconds. The electroporation pulse will be repeated. The suspension will be incubated at 18° C. for 1 to 24 hours. Uptake of PNA into the sperm will be verified by fluorescence microscopy.

The labeled sperm cells will be separated from the unlabeled sperm cells under flow using a FACSVantage SE with DiVa option flow cytometer with conditions as in Example 5. Selective binding of the PNA to the Y chromosome in the cells of the labeled fraction will be demonstrated by a flow cytometry histogram. At least 70% of the cells in the labeled fraction are expected to contain the Y chromosome. At least 70% of the cells of the unlabeled fraction are expected to contain the X chromosome.

Example 7: In Vitro Fertilization of Porcine Eggs with X or Y Chromosome-Enriched Boar Semen Viable boar sperm cell fractions labeled with CY3-PNA or unlabeled, as described in Example 6, were used to fertilize porcine eggs. About 1.5 to 2 hours before preparing the semen, one plate or dish containing 5 to 10 mL of TALP media and one plate or dish containing 5 to 10 mL of FERT media (TALP+caffeine) were prepared and placed in an incubator 38.5° C. for at least 1.5 hours to equilibrate. Additionally, approximately 30 mL of semen saline (0.9% saline+BSA) was placed in a hood to warm to room temperature. Sperm vision counting chambers were warmed.

To prepare the semen, 2 to 3 mL of the X or Y chromosome-enriched sperm cell fraction was brought up to 10 mL with semen saline (0.9% saline+BSA). The suspension was centrifuged at 800×g for 3 minutes. The semen saline was pulled down to the sperm pellet, the volume brought up to 10 mL with fresh semen saline, the pellet resuspended in fresh saline, and the suspension centrifuged. The washing procedure may be repeated for a total of three times. The final sperm pellet was resuspended in 3 mL of TALP, mixed gently, and a small sample was removed for subsequent sperm motility and concentration determination.

To prepare frozen-thawed X or Y chromosome-enriched sperm cell fraction, a frozen straw of semen (0.5 cc) was placed in a 50° C. water bath for 10 seconds. The thawed sperm was then layered over a density gradient and centrifuged at 350×g for 10 minutes. The pellet was washed once in 2 mL of Cellguard (Minitube, Verona, Wis., U.S.A.) and centrifuged at 200×g for 10 minutes. The pellet was diluted and mixed gently in 1 mL of TALP media, and a small sample was removed for subsequent sperm motility determination. Sperm motility and concentration was determined using Sperm Vision (Minitube of America, Verona, Wis., U.S.A).

To fertilize oocytes, 10 µL of sperm in FERT media (at a concentration of $2.5 \times 10^5$ sperm/mL) was added to a 500 µL well containing 50 oocytes. In vitro fertilization of porcine oocytes is also described in Rath et al. (J. Anim. Sci. 77:3346-3352 and Long, et al. (1999) Theriogenology 51:1375-1390), each of which is incorporated herein by reference in its entirety.

Example 8: Generation of a CY3-Labeled Peptide Nucleic Acid (PNA) Conjugate and Use to Identify Male and Female Sperm Synthetic DNA mimics conjugated to a fluorescent dye were used for in situ detection of Y chromosomes in metaphase preparations of bovine somatic cells and spermatozoa. Using male bovine somatic cells and the Y-chromosome as a template, a synthesis a CY3-conjugated PNA was designed and custom synthesized.

A PNA designated "Sequence K" was designed to bind to the target sequence shown in SEQ ID NO: 11. SEQ ID NO: 11 is a 14-nucleotide sequence at nucleotide positions 562 to 576 of the GSTRS shown in SEQ ID NO: 10. SEQ ID NO. 10 is a bovine Y chromosome sequence thought to be repeated 60,000 times (Perret, J. et al., 1990. *A polymorphic satellite sequence maps to the pericentric region of the bovine Y chromosome*; Genomics Vol 6 (3) pp 482-490). The PNA probe designated "Sequence K" was custom synthesized with a CY3 fluorescent molecule linked to the 5'-end by an ester bond: CY3-OO-AGC CCT GTG CCC TG Flow cytometry generated sexed bull sperm were evaluated with the PNA probe (Sequence K) for accuracy of scoring. By testing different labeling conditions, it was found that brief incubation of metaphase chromosomes with the PNA produced a localized signal on the Y-chromosome. The Y sorted sperm population showed labeling with the PNA probe in 104 signals on sperm heads out of 118 counted. The X sorted population showed labeling with the PNA probe in 8 signals on sperm heads out of 119 counted. In other tests, no signals were present when chromosomes of bovine female somatic cells were incubated with the PNA probe.

The PNA signals present in about 50% of sperm were found to consist of a single, centrally-located, round fluorescent dot in the sperm head. Unsorted bull sperm provided 23 signals out of 43 sperm heads (53.4%). The PNA probe was also found to produce signal in male bovine somatic cell lines and in embryos.

Example 9: Sex Determination of Bovine Embryos Using Bovine Blastomeres Recovered Via Biopsy A biopsy (n=5 to 8 blastomeres, pellucida-free) was taken from a blastocyst-stage embryo washed with phosphate buffered saline (PBS) and transferred onto a plastic slide. Cells were completely air-dried and heated on the slide to 60° C. for 1 minute. Cells were fixed by immersion in a solution containing 75% methanol and 25% acetic acid for 5 minutes. 2 µL of Buffer 1 containing 0.2M KCl and 0.2M NaOH, with the final pH being adjusted to 13.0 with 3 M NaOH, was added for 20 seconds, before 250 µL of a Tris-EDTA buffer with 10 mM KCl was added to neutralize Buffer 1. The slide was drained and to the cells were added 250 µL of the peptide nucleic acid probe SEQUENCE K conjugated to a fluorescent dye (CY-3) at the 5' end in 50% water/50% DMSO, which targets the unique Y-chromosome specific sequence SEQ ID NO. 11. After 5 minutes of incubation the cells were washed and 60 µL, mounting medium containing SlowFade (commercially available from Invitrogen) and DAPI (a DNA stain). Y-chromosomes were detected as a bright spot within the blastomere nuclei. The absence of signal indicated female embryonic DNA. After approximately 75 minutes of incubation with the probe on the slide the embryo gender was detected. The accuracy of the biopsy sexing procedure was demonstrated by parallel gender determination of the same embryo using an established PCR method designed for the bovine amelogenin locus. Based on 18 in vitro produced bovine embryos generating a result for both assays, there was a 94.4% match (17/18) of gender assignment.

It is to be understood that the invention is not limited in its application to the details of construction and the arrangement of components set forth in the foregoing description or illustrated in the drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. The use of the terms "a" and "an" and "the" and similar referents in the context of describing the invention are to be construed to cover both the singular and the plural, unless otherwise indicated herein or clearly contradicted by context Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method for separating a population of sperm cells, the method comprising:
   a) contacting the population of sperm cells with a labeled oligonucleotide moiety capable of binding a gender-specific tandem repeat sequence on either the Y chromosome or the X chromosome in a portion of the population of sperm cells to provide a labeled fraction and an unlabeled fraction, wherein the gender-specific tandem repeat sequence contains a target sequence having consecutive purine sequences or consecutive homopyrimidine sequences, wherein the target sequence of the gender-specific tandem repeat sequence has about 12 to about 24 nucleotides, wherein the gender-specific tandem repeat sequence is repeated at least 50 times on the respective chromosome of the labeled fraction, wherein the labeled oligonucleotide moiety comprises a triplex forming oligonucleotide moiety that binds to the target sequence, and wherein the labeled oligonucleotides moiety comprises a CY3 dye linked to a 5'-end of the triplex forming oligonucleotide with an ester bond;

b) detecting a signal that distinguishes the labeled fraction and the unlabeled fraction; and c) separating the labeled fraction from the unlabeled fraction forming a separated labeled fraction and a separated unlabeled fraction, wherein at least about 40% of each of the separated labeled fraction and the separated unlabeled fractions contain viable sperm cells that can be used for in vivo or in vitro fertilization.

2. The method of claim 1, wherein the oligonucleotide moiety comprises a purine triplex forming oligonucleotide, a pyrimidine triplex forming oligoneucleotide, or an OligoTRIP.

3. The method of claim 1, wherein a plurality of oligonucleotide moieties bind to the gender-specific tandem repeat sequence in step (a).

4. The method of claim 1, wherein the oligonucleotide moiety further comprises a detectable label chosen from a fluorescent tag, a heavy density tag, a magnetic tag, a nanoparticle, and combinations thereof.

5. The method of claim 1, wherein the gender-specific tandem repeat sequence comprises a polynucleotide having at least 80% identity to SEQ ID NO:1, a polynucleotide having at least 80% identity to SEQ ID NO:2, a polynucleotide having at least 80% identity to SEQ ID NO:3, or a polynucleotide having at least 80% identity to SEQ ID NO:4.

6. The method of claim 5, wherein the oligonucleotide moiety comprises sequence C (SEQ ID NO:14) or sequence D (SEQ ID NO:15).

7. The method of claim 5, wherein the gender-specific sequence comprises SEQ ID NO:2 or SEQ ID NO:3.

8. The method of claim 5, wherein at least 70% of the cells of the labeled fraction comprise a Y chromosome and at least 70% of the cells of the unlabeled fraction comprise a X chromosome.

9. The method of claim 5, wherein at least 70% of cells of the labeled fraction comprise an X chromosome and at least 70% of the cells of the unlabeled fraction comprise a Y chromosome.

10. The method of claim 1, wherein at least 50% of the cells of the labeled fraction or the unlabeled fraction are viable after step (c).

11. The method of claim 1, wherein separating the cells in step (c) comprises separation by flow cytometry, centrifugation, or magnetic force.

12. The method of claim 1, wherein the gender-specific tandem repeat sequence comprises a telomeric sequence.

13. The method of claim 1, wherein the gender-specific tandem repeat sequence is from about 2,000 to about 10,000 nucleotides.

14. The method of claim 1, wherein the labeled oligonucleotide is from about 12 to about 24 nucleotides.

15. The method of claim 1, wherein the sperm cells comprise mammalian sperm cells selected from bovine, porcine, canine, and equine sperm cells.

16. A method for separating a population of sperm cells having an X chromosome and a Y chromosome, the method comprising:

a) contacting the population of sperm cells with a labeled oligonucleotide moiety capable of binding to a gender-specific tandem repeat sequence that is repeated on either the Y chromosome or the X chromosome in a portion of the population of sperm cells to provide a labeled fraction and an unlabeled fraction, wherein the gender-specific tandem repeat sequence contains a target sequence having consecutive purine sequences or consecutive homopyrimidine sequences, wherein the target sequence of the gender-specific tandem repeat sequence has about 12 to about 24 nucleotides, wherein the labeled oligonucleotide moiety is capable of binding to a major groove of a DNA duplex of the gender-specific tandem repeat sequence in the labeled fraction, and wherein the gender-specific tandem repeat sequence is repeated at least 50 times on the respective chromosome of the labeled fraction, wherein the labeled oligonucleotide moiety comprises a triplex forming oligonucleotide moiety that binds to the target sequence, and wherein the labeled oligonucleotides moiety comprises a CY3 dye linked to a 5'-end of the triplex forming oligonucleotide with an ester linkage;

b) detecting a signal that distinguishes the labeled fraction and the unlabeled fraction; and c) separating the labeled fraction from the unlabeled fraction forming a separated labeled fraction and a separated unlabeled fraction, wherein at least about 40% of the labeled fraction contains viable sperm cells that can be used for in vivo or in vitro fertilization.

* * * * *

SEQUENCE LISTING

<160> NUMBER OF SEQ ID NOS: 20

<210> SEQ ID NO 1
<211> LENGTH: 3832
<212> TYPE: DNA
<213> ORGANISM: Sus scrofa

<400> SEQUENCE: 1

```
gaattctcat taggtccctt atgtgtaggt ggtggaaaag atgttgatct cggagtcaaa        60
tgtgtgatca tgtagaacgc agtggcaatg ggatggttat ctgtcagtgt gaagggctga       120
gaatggtaag gtatgggtgc acggtgtaag gtgaaatatc tccatacaag aagcggagtt       180
acttcctgcg caaagaattt gtagttgata ggagtttgga agactgatgg agaatctcgg       240
ttaaagaatt tgactgctct cctggctgag atttgccaac ctggaccagc acagataacc       300
ttggctgagg aggattcgag agaatgtgaa ggaggaagaa gccgagagag agagagagat       360
gaaatttgga tacaagccac attccagggc acagtttcat tcccaagccc ttgtctgtgt       420
ttccggggac tattagacac gaaggctgta tcaggactct tgcatgagat tttcactcgt       480
tcttggcctt tctctagaag tacgtcgatt gccagcagtc cgtgcttggc acccatgtct       540
tctcaaagta cacgaggtgt gggtcagtta aatgacaccc tatattttcc ctaagcggca       600
aagacactgc ctattgaaat ggcagctcat agggtgtcct tcctcagtcg ttccttgatt       660
tcattgtcca ggggccttta gtttgggtgt ttggaatgat atcttttctc tccaaaagag       720
attctatact gtgtattcgt gtgaagcagt gactgagaaa gcacttgacc ctgaagtgct       780
gcacatgtta tcagatatcc atcatgatag agaaaattgg gctcccagt gtgtggagtt       840 gccttccttc ggaaaggtgc agtcccgagg gtggccatgg ttctgatatc atgcccatgg       900
agccttgtgc ccaaacaacc tctctgtgag aaaagaggtg tgtgatgggc catatgtggg       960
aaagtctcac cctcaaacct tgagagttaa aggatggaca cctgagctc ttgctctgga      1020 ggtctgtcga agttgatgga aaggaggatc catcagatgg gtggtccttt tggatgaaca      1080
ctattatcgc catctgtaga ctcatagcca ccactctcat caggctccca agctcaatgt      1140
ggattctaga ggcttggtgt ttgaacatgt gatatcttca ggggatccgt gggcagaata      1200
cctcacggga gttcctccat gtgaaaaag agttgtgctt cagggccatt tgaaacaata      1260
cctccgcgcg cacaaagaag gaatccatgc ccgaatgctc tccaccaagc gtgaggccct      1320
ggatgtaacc cctcaaagag actttcccaa tggggcattt tcagctccac acttctgaat      1380
ccatatttcc atagcctaag ccacagggga gccctccaaa cagaggcctt taaaccaaga      1440
```

-continued

```
tgtatccggt ctatttcagg tgccttttcc acaggtggat aagaacaagc cctcccactc    1500
attgagtgac ttactgggag tgtggtgcct ggggccaggg ccagtgtgtt tgttctatct    1560
acagtcataa ggaaggaagc tgggacgatg atctgatctt ccaggagcgc tgtgatgatg    1620
cctgcaatgt gagggtattg aaagttccct cctggaaggg agtgggctct gtccctgaca    1680
ctcctgaggc tagagaatga ggaggtctaa tccatagaga ctggtttttg ttgacagaca    1740
tcttgcactc tgggctcttg ttggccagcc cactcgccaa ggatgctcag accattgttt    1800
ggatgcccag tcattgagac atgaagagtc ctagacatca tattctatat cccctaagaa    1860
cgagtccaga gatcctcaca tgagcaaatc caccatacct catggaccag gtagggaatg    1920
ctgcagatca gcactttctt gggagagcac tcatgggaac gttgtttcaa gtgcgttgca    1980
ctctgcgtcc aatatgggac cctcgagacc gaagtacata tgaagtggtc agcgtgtcca    2040
taggaaggga tgactatggg aagtatggtt taaggctgac ctagttgggg tgtctccaca    2100
cagcacagga agtctttcag gaccacggaa tttatatgcg atcagaccta ggatgacagg    2160
gagaaaaggc tggggataa cttggacgat tctcttggca aatatatttg atccattatt    2220
accccaggtc gaattgtagc aggaggatac aggagaaatt gaaggggggc aaggggaga    2280 gtgagagagc tagagagaag gagatgaaaa gaaggcgaga gagaggtaaa ggagctgttg    2340
tttcaagcaa ctgtcaatgg caggataatt tctccaagga cgtgtctttc tttaaggtgg    2400
ctagcacaca aatgggacaa accagcacac ttgtcccaga gtcttctctc cttcaaggcc    2460
tgacgcccac attgtgtcta ttacaatccc tgctccatcc tggaagacag gtttgaaagc    2520
cttgctgtgg tccctctatc ttctccaatg gcatggggtg gaaatcagag taagagatat    2580
tccatagttt ccttcagggg aaaagcctcc tcccatggaa agagatgctc gtgtgttgtt    2640
cttcctccat cggccattgt tttcctgttc aggctccgtg gggagtgggt ctttttcaat    2700
gccatatttt ctttcctaat gaggttgtag actgtgtatt cctgggaagc agttttggaa    2760
ccaccgtgtt gagcctgaca cacgttcagg gaagaggca tccttctgta gagagcaggt    2820
gggcacagag gaggtggagt tgccttccat ctagaagttc aggcccaatg gttgccatgg    2880
caagggcatg ttgcgcacca agtattgtga cacaacacac cgtatgtgag aagagaggcg    2940
agggatgggc ccaaagtggg aagctctcac cgtcacccccc aattggttgt acctcgggca    3000
gcctgatctc atgatctgga ggtatgttga tactaaatga aacgaggatc cattggatgt    3060
attggacaat tggatgataa gtagtatttc cagcattctt ctcatggcca ccattctcat    3120
caggctgctg aggaaatagg cactgctcag gcttgctttt ggatgatgat ccatttgaaa    3180
gggaccagtg agcctatccc ttccagtctt ttccaacagg gaaaaaaga ctcctaagta    3240 tgaccgggat gagaaatctc attccagatc tcaaagcctg aaaattggcc actcagcctt    3300
ccaaaaaaga cgaggccctc aacatcaacc cttacgaaat actggaatgg gggcaaggac    3360
cattccttgc ttcggaacgt acacgtccat agatgaaatc acaaactagc tctccacagt    3420
aacaaatttc ccaagaatga agctgggata tgtctggtgg gtatttcaca ggttgataag    3480
aataagtcct gtctaaaggg gtgctggatg gaagtggggt gactagttcc actgctggct    3540
gtttgtgggg tacacagttg tcaggaattt aaggagtctc tcttgttatc ttccgtgagc    3600
cctgtggtga gggctcccct tgggcaggac ttgaggtttc gctcttggac gagaggggcc    3660
tctggcctgc caatgagggg tctagagaag gaggaggatt gtcccaaatg gagactggtt    3720
tgaggggacc gaatcctgga actctgtccc attgtcattc agaccctgct gaagggtgct    3780 cagaccccctt cttagatgcc aaatcactga gacatggaga ggcagagaat tc          3832
```

<210> SEQ ID NO 2
<211> LENGTH: 16
<212> TYPE: DNA
<213> ORGANISM: Sus scrofa

<400> SEQUENCE: 2
gagagagaga gagaga                                                      16

<210> SEQ ID NO 3
<211> LENGTH: 20
<212> TYPE: DNA
<213> ORGANISM: Sus scrofa

<400> SEQUENCE: 3
tctagagaag gaggaggatt                                                  20

<210> SEQ ID NO 4
<211> LENGTH: 205
<212> TYPE: DNA
<213> ORGANISM: Sus scrofa

<400> SEQUENCE: 4
ctcccttctg tctttatccc catctcaaca atccgaagtg attcgactga ggcgttcccg      60
ttgtggctca gcggtaatga acctgactag gatccatgag gttgtgagtt gtatccctgg     120
ccttgctccg tgggttaagg atccggtgtt gctgagagct gtggtgcagg tcgcagatat     180
atcttggatc ccctgttgct gtggc                                           205

<210> SEQ ID NO 5
<211> LENGTH: 1399
<212> TYPE: DNA
<213> ORGANISM: Bos taurus

<400> SEQUENCE: 5
aattcaggct gcctcttgtg ttggcccagg caagtccaat cttccattcg agttgcgaag      60
gaaagctggg gattgctctc gagtgactgc agggccaata gacctcatct aggcttgtgt     120
ccagaagcca atgttcctct ccaggggcga cagggatctc ggggttgcat tccagacgca     180
cccggggaga caggcattca tctcgagtgg aagcaaagaa ccccgctctg ctctcgaatt     240
gtgacgggta tctcttggag ctcactgggt ggactcaagg gagtcaagcc tcctgaggcg     300
tttggagaga ggtcgcgaga ttggtctcta ggccatgcag gagacgaagg ccctcatctc     360
tcgatgacgg cccaatctcg gggttgttct cgagcggcgg ccccagtgtg cggtttctca     420
cgaggtacaa cggcgaggtc agtgagcctc tcgtggggcg ccaggaagt cgggtctcca      480 tgcgagtggc gaggggagc gcgtcattgc tcccagccca tggtagggga atctggcctc     540
gagacgtgtt gaagaaggtc tctcgagggc tttcccgggt tgaggcagga aaccctgggt     600
tccctcgact tgtgcaggtg acctcagggg gcttctcacg gtggctctga aagccaggg      660 aaactggagg tgggagggc ctcttgggac tccactgggc ttggtgcatt ggaagagggc      720
ctcatctcca gtggaggcag gaaccgcagg tacctctgat ttcagactcc gatcgcaggg     780
tccctgcaga ctggggacag gagagtcagg cctcgtcttg ggttgaggca tggaactccg     840
cttgcctctc gagatgtccc cggggagaga ggccgcttgt cgagctgtat ttggaacctg     900 gggtttttc cgaacgatgc acggaaaaac tgccccctcg tgttgacttc attcacaggc     960
tggagttcgg agaggtgtcc gggcatcggg ttcttatcaa gaggggaccg ggaaatcggg    1020

```
gtcctacgga atgtggaacc acccacgagg ccacgtctgg aatgtcttcg tgagaccggc    1080
ctcatcctga ggtgcgaccg gaaggtcggg aaccccttcc agacaaagca ggggagtcga    1140
ccctcctgtc cagatcagga ggggagaaag ggctcagagg aggggggtgcc ggaaaacctc   1200 agtgttcctc tcgagggaga ccgggatttc ggggaactttt gtgggtcgca tcaagggtgc   1260
caagtgccct ttcgacctcc aattcctaac gtgggacttc tcctgaggcg ctgtagcccc    1320
aaagggcttc atcttgcgat gacggggggag ccacgtggtt tttctcgagt tacggcggga   1380
ttctcaagtt gcgacgggg                                                 1399
```

```
<210> SEQ ID NO 6
<211> LENGTH: 16
<212> TYPE: DNA
<213> ORGANISM: Bos taurus

<400> SEQUENCE: 6
aggaggggag aaaggg                                                      16
```

```
<210> SEQ ID NO 7
<211> LENGTH: 313
<212> TYPE: DNA
<213> ORGANISM: Sus scrofa

<400> SEQUENCE: 7
gaggaaagtt gcactttcac ggacgcagcc tcccagatgg gccctagctg ggtccctccc      60
tacctgtaga aaggtgaggt ggtggggcca cttgccacac aaggcatatt ctggccccat     120
ccgcctcctc cctgaagtag agcacgtttg gagttggttt ccagctctag caatgacctg     180
caaagcacca gtgcacaggg agcaggaggc agcccagacc ctccttgttc ctatggcgag     240
caatgggcta ggggagaaac cagaaagcgc tgctttcctg acgaaacacg cattgggctg     300
agcttggttt ccc                                                       313
```

```
<210> SEQ ID NO 8
<211> LENGTH: 14
<212> TYPE: DNA
<213> ORGANISM: Sus scrofa

<400> SEQUENCE: 8
tccgcctcct ccct                                                       14
```

```
<210> SEQ ID NO 9
<211> LENGTH: 15
<212> TYPE: DNA
<213> ORGANISM: Sus scrofa

<400> SEQUENCE: 9
ctcccttctg tcttt                                                      15
```

```
<210> SEQ ID NO 10
<211> LENGTH: 1184
<212> TYPE: DNA
<213> ORGANISM: Bos taurus

<400> SEQUENCE: 10
atgcaagccc gggatctcag ccctgtggtc tgggaactgt gaaaccggct tgagtatgtg      60
tgctgttatc agcactgtgc cctggcgact ctgatactgg tttgtgttca tgtgtgtgtg     120
tgtgtgtgtg tgtgttgctg ttctcagccc tgtgccctgg cgattgtgca accagtatct    180
gtatgcctgt gtgtgtgtgt gtgtgtgtgt gtgtgtgtgt gtgtgctgtt ctcaacccat    240
```

```
tgccctggcg attgttcaac cagtttgtgt atatgtgtgt gtagatgtgt gtgccatcct      300
gagccttgtg ccctggcaac tggggaaacg gtgtgtgtgt gttgtgtgtc tgtgtgtgtg      360
ctgatttcag ccatgtgccc ttctgactgt gcaactggtt tgtgtgtgtg tgcacgcgat      420
tctcacctct gtgtcctggc gactgtgtaa ccgtttgtgt gtgtgagtgt gtgtaagtgt      480
gtgctctttt cagccctgtt cctagagac tgtggaaccg gttggtgtgt gtgtgtgtct      540
gtgtgtgtgt gtgccattct cagccctgtg ccctggcgac tgtgcaatat tttgtcgtgt      600
gtgtgtgtgt gtgtatttgt gtgtgcaatt cacagccctg ttccctggcg actgtgcaag      660
cagattgttg cgtatgtttc tgtgtgtgtg tgtgtgtgtg tgtgtgtgta tgtgctgttc      720
tcagccctgt gccctggcaa ctgtgaaacc ggtttgtatg tgtgtgtgtg tttgtgtgtg      780
ccattcacag ccctgtgccc tggcgactgt gcaagcagtt tgtgtgtgca tgtgtctgtg      840
tgtgtatgtg tctgtgtgtg catgtgtctg tgtgtgttat atgctgttct cagccctgtg      900
ccctggcgac tgagaaaccg gttgtgtgtg tgtgtgtgtg tgtgtgtgtg tgtgccagtt      960
tcagccctgt gccttggtac tgtgcaagtg gtttgtgtgt gtgtgtgtag tgtatatgtg     1020
tgtgtgtggt ttgaccagtt ttcagccctg tgccttagtg actgtgtaac tggtgtgtgt     1080
gtgtgtgtgt gtgtgtgtgc tcttctcagc cctgtgccct gttgactgtg caagcggttt     1140
gtctgtgtat gtgagtgggt gctgttctca tgcctgtgca ctgg                      1184

<210> SEQ ID NO 11
<211> LENGTH: 15
<212> TYPE: DNA
<213> ORGANISM: Bos taurus

<400> SEQUENCE: 11
agccctgtgc cctgg                                                        15

<210> SEQ ID NO 12
<211> LENGTH: 16
<212> TYPE: DNA
<213> ORGANISM: Artificial Sequence
<220> FEATURE:
<223> OTHER INFORMATION: Oligonucleotides moieties

<400> SEQUENCE: 12
tctctctctc tctctc                                                       16

<210> SEQ ID NO 13
<211> LENGTH: 12
<212> TYPE: DNA
<213> ORGANISM: Artificial Sequence
<220> FEATURE:
<223> OTHER INFORMATION: Oligonucleotides moieties

<400> SEQUENCE: 13
tctctctctc tc                                                           12

<210> SEQ ID NO 14
<211> LENGTH: 16
<212> TYPE: DNA
<213> ORGANISM: Artificial Sequence
<220> FEATURE:
<223> OTHER INFORMATION: Oligonucleotides moieties

<400> SEQUENCE: 14
ctctctctct ctctct                                                       16
```

```
<210> SEQ ID NO 15
<211> LENGTH: 15
<212> TYPE: DNA
<213> ORGANISM: Artificial Sequence
<220> FEATURE:
<223> OTHER INFORMATION: Oligonucleotides moieties

<400> SEQUENCE: 15
tctcttcctc ctcct                                                    15

<210> SEQ ID NO 16
<211> LENGTH: 14
<212> TYPE: DNA
<213> ORGANISM: Artificial Sequence
<220> FEATURE:
<223> OTHER INFORMATION: Oligonucleotides moieties

<400> SEQUENCE: 16
tcctcccctc tttc                                                     14

<210> SEQ ID NO 17
<211> LENGTH: 14
<212> TYPE: DNA
<213> ORGANISM: Artificial Sequence
<220> FEATURE:
<223> OTHER INFORMATION: Oligonucleotides moieties

<400> SEQUENCE: 17
tccctcctcc tcct                                                     14

<210> SEQ ID NO 18
<211> LENGTH: 10
<212> TYPE: DNA
<213> ORGANISM: Artificial Sequence
<220> FEATURE:
<223> OTHER INFORMATION: Oligonucleotides moieties

<400> SEQUENCE: 18
ggtggtgggt                                                          10

<210> SEQ ID NO 19
<211> LENGTH: 17
<212> TYPE: DNA
<213> ORGANISM: Artificial Sequence
<220> FEATURE:
<223> OTHER INFORMATION: Oligonucleotides moieties

<400> SEQUENCE: 19
ctcccttctg tctttat                                                  17

<210> SEQ ID NO 20
<211> LENGTH: 14
<212> TYPE: DNA
<213> ORGANISM: Artificial Sequence
<220> FEATURE:
<223> OTHER INFORMATION: Oligonucleotides moieties

<400> SEQUENCE: 20
agccctgtgc cctg                                                     14
```